United States Patent
Prencipe et al.

(10) Patent No.: US 9,918,918 B2
(45) Date of Patent: Mar. 20, 2018

(54) COMPOSITIONS FOR TOOTH-WHITENING COMPRISING A BLEACHING AGENT AND A BASIC AMINO ACID, AND METHODS AND DEVICES FOR APPLICATION THEREOF

(75) Inventors: Michael Prencipe, Princeton Junction, NJ (US); Richard Scott Robinson, Belle Mead, NJ (US); Rajnish Kohli, Hillsborough, NJ (US); Richard J. Sullivan, Atlantic Highlands, NJ (US)

(73) Assignee: Colgate-Palmolive Company, New York, NY (US)

( * ) Notice: Subject to any disclaimer, the term of this patent is extended or adjusted under 35 U.S.C. 154(b) by 1218 days.

(21) Appl. No.: 12/866,780

(22) PCT Filed: Feb. 6, 2009

(86) PCT No.: PCT/US2009/033306
§ 371 (c)(1),
(2), (4) Date: Aug. 9, 2010

(87) PCT Pub. No.: WO2009/100277
PCT Pub. Date: Aug. 13, 2009

(65) Prior Publication Data
US 2010/0322988 A1  Dec. 23, 2010

Related U.S. Application Data

(60) Provisional application No. 61/027,429, filed on Feb. 8, 2008.

(51) Int. Cl.
*A61K 8/44* (2006.01)
*A61Q 11/00* (2006.01)
*A61K 8/22* (2006.01)

(52) U.S. Cl.
CPC .................. *A61K 8/44* (2013.01); *A61K 8/22* (2013.01); *A61Q 11/00* (2013.01)

(58) Field of Classification Search
None
See application file for complete search history.

(56) References Cited

U.S. PATENT DOCUMENTS

| | | |
|---|---|---|
| 3,535,421 A | 10/1970 | Briner et al. |
| 3,678,154 A | 7/1972 | Widder et al. |
| 3,925,543 A | 12/1975 | Donohue |
| 3,932,605 A | 1/1976 | Vit |
| 3,932,608 A | 1/1976 | Anderson et al. |
| 3,943,241 A | 3/1976 | Anderson et al. |
| 3,988,434 A | 10/1976 | Schole et al. |
| 4,011,309 A | 3/1977 | Lutz |
| 4,022,880 A | 5/1977 | Vinson et al. |
| 4,025,616 A | 5/1977 | Haefele |
| 4,042,680 A | 8/1977 | Muhler et al. |
| 4,064,138 A | 12/1977 | Saari et al. |
| 4,100,269 A | 7/1978 | Pader |
| 4,108,979 A | 8/1978 | Muhler et al. |
| 4,108,981 A | 8/1978 | Muhler et al. |
| 4,146,607 A | 3/1979 | Ritchey |
| 4,154,813 A * | 5/1979 | Kleinberg ...................... 424/48 |
| 4,160,821 A | 7/1979 | Sipos |
| 4,216,961 A | 7/1980 | Curtis et al. |
| 4,225,579 A | 9/1980 | Kleinberg |
| 4,259,316 A | 3/1981 | Nakashima et al. |
| 4,269,822 A | 5/1981 | Pellico et al. |
| 4,305,928 A | 12/1981 | Harvey |
| 4,335,102 A | 6/1982 | Nakashima et al. |
| 4,339,432 A | 7/1982 | Ritchey et al. |
| RE31,181 E | 3/1983 | Kleinberg et al. |
| 4,466,954 A | 8/1984 | Ichikawa et al. |
| 4,477,429 A | 10/1984 | Silbering et al. |
| 4,528,181 A | 7/1985 | Morton et al. |
| 4,532,124 A | 7/1985 | Pearce |
| 4,538,990 A | 9/1985 | Pashley |
| 4,645,662 A | 2/1987 | Nakashima et al. |
| 4,656,031 A | 4/1987 | Lane et al. |
| 4,725,576 A | 2/1988 | Pollock et al. |
| 4,885,155 A | 12/1989 | Parran, Jr. et al. |
| 4,997,640 A | 3/1991 | Bird et al. |
| 5,096,700 A | 3/1992 | Siebel et al. |
| 5,192,531 A * | 3/1993 | Gaffar et al. ................... 424/52 |
| 5,286,480 A | 8/1994 | Boggs et al. |
| 5,334,617 A | 12/1994 | Ulrich et al. |
| 5,370,865 A | 12/1994 | Yamagishi et al. |
| 5,376,006 A | 12/1994 | Fischer |
| 5,639,795 A | 6/1997 | Friedman et al. |
| 5,693,795 A | 6/1997 | Friedman et al. |
| 5,746,598 A | 5/1998 | Fischer |

(Continued)

FOREIGN PATENT DOCUMENTS

| | | |
|---|---|---|
| CN | 1227483 | 9/1999 |
| EP | 2111135 | 10/2009 |

(Continued)

OTHER PUBLICATIONS

US 5,989,525, 11/1999, Kleinberg et al. (withdrawn)
DenClude®, 2004, Ortek Therapeutics Inc., Packaging with ingredient list, launched Dec. 2004.
Fedotov, 2007, The Big Dictionary of Medical Terms, p. 340.
ISR and Written Opinion for PCT/US09/033306 dated Sep. 24, 2009.
ProClude®, 2002, Ortek Therapeutics Inc., Packaging with ingredient list, launched Jul. 2002.
Machado et al. CaviStat Confection Inhibition of Caries in Posterior Teeth, Abstract, 83rd Session of the American Association for Dental Research, Mar. 21-24, (2007), New Orleans, LA.
Chatterjee et al,. Bacterial Acidification and CaviStat Alkalinization of Occlusal Fissure pH, Abstract, 83rd Session of the American Association for Dental Research, Mar. 9-12, (2005), Baltimore, MD.
Kleinberg I., A Mixed-Bacteria Ecological Approach to Understanding the Role of the Oral Bacteria in Dental Caries Causation: An Alternative to *Streptococcus* Mutans and the Specific-Plaque Hypothesis, Crit. Rev. Oral Biol. Med,. 12(2): 108-125 (2002).

(Continued)

*Primary Examiner* — Johann R Richter
*Assistant Examiner* — Katherine Peebles

(57) ABSTRACT

The present invention provides tooth-whitening compositions comprising a bleaching agent and a basic amino acid, together with devices for application thereof, and methods of use therefor.

23 Claims, No Drawings

(56) References Cited

U.S. PATENT DOCUMENTS

| | | | |
|---|---|---|---|
| 5,747,004 A | 5/1998 | Giani et al. | |
| 5,762,911 A * | 6/1998 | Kleinberg | A61K 8/19 424/49 |
| 5,855,870 A * | 1/1999 | Fischer | A61C 5/00 424/49 |
| 5,879,691 A | 3/1999 | Sagel et al. | |
| 5,891,453 A | 4/1999 | Sagel et al. | |
| 5,894,071 A | 4/1999 | Merz et al. | |
| 5,906,811 A | 5/1999 | Hersh | |
| 5,922,346 A | 7/1999 | Hersh | |
| 5,997,301 A | 12/1999 | Linden | |
| 6,136,297 A * | 10/2000 | Sagel | A61K 8/0208 106/35 |
| 6,166,102 A | 12/2000 | Ahn et al. | |
| 6,217,851 B1 | 4/2001 | Kleinberg et al. | |
| 6,270,890 B1 | 8/2001 | Curtis et al. | |
| 6,277,458 B1 | 8/2001 | Dirksing | |
| 6,289,904 B1 | 9/2001 | Suhonen et al. | |
| 6,416,745 B1 * | 7/2002 | Markowitz et al. | 424/49 |
| 6,436,297 B1 | 8/2002 | Leabeau et al. | |
| 6,436,370 B1 | 8/2002 | Kleinberg et al. | |
| 6,453,912 B1 | 9/2002 | Antler | |
| 6,488,961 B1 | 12/2002 | Robinson et al. | |
| 6,500,408 B2 * | 12/2002 | Chen | 424/53 |
| 6,524,588 B1 | 2/2003 | Kleinberg et al. | |
| 6,558,654 B2 | 5/2003 | McLaughlin | |
| 6,616,933 B1 | 9/2003 | Breton et al. | |
| 6,648,644 B1 | 11/2003 | Flemmig et al. | |
| 6,669,930 B1 | 12/2003 | Hoic et al. | |
| 6,727,285 B1 * | 4/2004 | Haik, Jr. | 514/565 |
| 6,730,316 B2 | 5/2004 | Chen | |
| 6,805,883 B2 | 10/2004 | Chevaus et al. | |
| 7,427,421 B2 * | 9/2008 | Dewis et al. | 426/534 |
| 9,242,125 B2 | 1/2016 | Boyd et al. | |
| 2001/0006624 A1 * | 7/2001 | Witt et al. | 424/53 |
| 2002/0064504 A1 * | 5/2002 | Kleinberg et al. | 424/49 |
| 2002/0081360 A1 | 6/2002 | Burgard et al. | |
| 2003/0143315 A1 | 7/2003 | Pui et al. | |
| 2003/0170592 A1 * | 9/2003 | Chadwick et al. | 433/215 |
| 2003/0228264 A1 * | 12/2003 | Perna | A61C 19/066 424/53 |
| 2004/0101496 A1 | 5/2004 | Chen | |
| 2005/0038181 A1 | 2/2005 | Chopra et al. | |
| 2006/0032002 A1 * | 2/2006 | Bolton et al. | 8/405 |
| 2006/0140882 A1 | 6/2006 | Tambs et al. | |
| 2006/0246398 A1 | 11/2006 | Groll et al. | |
| 2007/0148213 A1 | 6/2007 | Ibrahim | |
| 2007/0154863 A1 | 7/2007 | Cai et al. | |
| 2007/0231276 A1 * | 10/2007 | Sharma et al. | 424/53 |
| 2007/0231277 A1 | 10/2007 | Sharma et al. | |

FOREIGN PATENT DOCUMENTS

| | | | |
|---|---|---|---|
| GB | 2354441 | | 3/2001 |
| JP | 07-258053 | | 10/1995 |
| JP | H08-151324 | | 6/1996 |
| JP | 2001-504083 | | 3/2001 |
| JP | 2006-506436 | | 2/2006 |
| KR | 10-2006-0081533 | | 7/2006 |
| RU | 2093137 | | 10/1997 |
| RU | 2192202 | | 11/2002 |
| RU | 2283081 | | 9/2006 |
| WO | WO 1997/032565 | | 9/1997 |
| WO | 1999040870 | | 8/1999 |
| WO | WO 00/078270 | | 12/2000 |
| WO | WO2002032961 | | 4/2002 |
| WO | WO-2004/039343 | * | 5/2004 |
| WO | WO 2004/045446 | | 6/2004 |
| WO | WO 07/061794 | | 5/2007 |
| WO | WO 07/117927 | | 10/2007 |
| WO | WO 2007/117926 | | 10/2007 |
| WO | WO 08/091935 | | 7/2008 |
| WO | WO 2009/100277 | | 8/2009 |
| WO | WO2009100267 | | 8/2009 |

OTHER PUBLICATIONS

Kleinberg I., A New Salvia-Based Anticaries Composition, Dentistry Today, vol. 18, No. 2, Feb. 1999.

Acevedo et al., "The Inhibitory effect of an arginine bicarbonate/calcium carbonate (CaviStat)-containing dentifrice on the develpoment of dental caries in Venezuelean school children", The Journal of clinical Dentistry, 2005, v.16, No. 3,pp. 63-70, ISSN 0895-8831.

Anonymous, "Toothpaste Focus," Oct. 1, 2006, Retrieved from http://www.dimensionsofdentalhygiene.com/uploadfiles/DDH/Magazine/2006/10_October/toothpastefocus.pdf.

Kugel et al., "The Art and Science of Tooth Whitening," Inside Dentistry, Sep. 1, 2006, Retrieved from http://www.dentalaegis.com/id/2006/09/focus-on-the-art-and-science-of-tooth-whitening.

Rosen, "A Successful Approach to Whitening Without Dentinal Sensitivity," Dentistry Today, Nov. 30, 2005, http://www.dentistrytoday.com/aesthetics/129.

* cited by examiner

COMPOSITIONS FOR TOOTH-WHITENING COMPRISING A BLEACHING AGENT AND A BASIC AMINO ACID, AND METHODS AND DEVICES FOR APPLICATION THEREOF

This application claims the benefit of U.S. Patent Application Ser. No. 61/027,429 filed Feb. 8, 2008, the contents of which are incorporated herein by reference.

BACKGROUND OF THE INVENTION

Teeth whitening products are known in art, and include products and methods which are sold over the counter, or performed professionally. One bleaching device uses a tray which holds a bleaching composition and is then applied to the teeth. See e.g., U.S. Pat. Nos. 5,746,598 and 5,376,006, the contents of which are incorporated herein by reference. Another bleaching device is in the form of a strip which is applied to a tooth surface. See e.g., U.S. Pat. Nos. 5,891,453, 6,436,297, 5,879,691, 6,277,458, 5,894,071, the contents of which are incorporated herein by reference. Other bleaching devices are liquid tooth whitening gels as described in U.S. Pat. No. 6,669,930, US Publication 2005/0038181 and WO 2002/032961, the contents of which are incorporated herein by reference. While use of such devices may cause tooth whitening, they do not generally address treating the oral cavity for other indications. Indeed, such devices may also worsen some oral conditions. For example, people wearing such devices may tend to keep their mouths open, thereby causing increased evaporation of saliva resulting in dry mouth.

While the use of such products may whiten teeth, there is a need to develop compositions which may simultaneously whiten teeth and treat the oral cavity, e.g., simultaneously reduce or inhibit formation of dental caries, reduce or inhibit demineralization and promote remineralization of the teeth, and/or treat dry mouth.

SUMMARY OF THE INVENTION

The compositions of the present invention can promote or improve oral health and/or systemic health, including cardiovascular health. e.g., by reducing potential for systemic infection via the oral tissues.

The present invention is directed to compositions and devices which deliver basic amino acids, e.g., arginine, to the oral cavity together with a whitening agent to whiten teeth, and, e.g., (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) clean the teeth and oral cavity, (xiii) immunize the teeth against cariogenic bacteria, (xiv) promote systemic health, including cardiovascular health, e.g., by reducing potential for systemic infection via the oral tissues, (xv) reduce erosion and/or (xv) treat, relieve or reduce dry mouth. Such compositions and devices may be used alone, or in conjunction with other basic amino acid containing compositions, e.g., dentifrice compositions to deliver a basic amino acid to the oral cavity.

Arginine and other basic amino acids have been proposed for use in oral care and are believed to have significant benefits in combating cavity formation and tooth sensitivity. It is believed that basic amino acids in the oral cavity are metabolized by certain types of bacteria, e.g., *S. sanguis* which are not cariogenic and which compete with cariogenic bacteria such as *S. mutans*, for position on the teeth and in the oral cavity. The arginolytic bacteria can use arginine and other basic amino acids to produce ammonia, thereby raising the pH of their environment, while cariogenic bacteria metabolize sugar to produce lactic acid, which tends to lower the plaque pH and demineralize the teeth, ultimately leading to cavities. Basic amino acids, e.g., arginine, moreover promote remineralization of the teeth, helping to repair erosion, and plugging microtubules implicated in dentinal sensitivity. Many patients complain of hypersensitive teeth following bleaching treatments, possibly because the whitening chemicals irritate the nerve endings in the microtubules.

The present invention thus includes Composition 1.0, a dental bleaching composition comprising
  a. an effective amount of a dental whitening agent capable of bleaching tooth surfaces in contact with the dental whitening agent, and
  b. a basic amino acid in free or salt form.

The present invention also includes the following compositions:
  1.1 Composition 1.0 wherein the basic amino acid is arginine, lysine, citrullene, ornithine, creatine, histidine, diaminobutanoic acid, diaminoproprionic acid, salts thereof and/or combinations thereof.
  1.2 Composition 1.0 or 1.1 wherein the basic amino acid has the L-configuration.
  1.3 Any of the preceding compositions wherein the basic amino acid is arginine.
  1.4 Any of the preceding compositions wherein the basic amino acid is L-arginine.
  1.5 Any of the preceding compositions comprising a basic amino acid is in salt form.
  1.6 Any of the preceding compositions comprising arginine phosphate.
  1.7 Any of the preceding compositions comprising arginine hydrochloride.
  1.8 Any of the preceding compositions comprising arginine percarbonate.
  1.9 Any of the preceding compositions comprising arginine bicarbonate.
  1.10 Any of the preceding compositions comprising from about 0.1% to about 50% by weight of the basic amino acid.
  1.11 Any of the preceding compositions further comprising a matrix material.
  1.12 Any of the preceding compositions wherein the dental whitening agent and basic amino acid is dispersed within the matrix material.
  1.13 Any of the preceding compositions further comprising carboxypolymethylene.
  1.14 Any of the preceding compositions further comprising a matrix material comprising reaction products of carboxypolymethylene,
  1.15 Any of the preceding compositions comprising polyvinylpyrrolidone.
  1.16 Any of the preceding compositions further comprising a matrix material having a stickiness and/or resistance to dilution by saliva such that when the dental composition is placed within a dental tray and the dental tray is positioned over the teeth the dental composition will retain the dental tray in position over the teeth, e.g., for at least about 1, 2, 3, 4, or 5 hours without significant pressure exerted by the dental tray.

1.17 Any of the preceding compositions further comprising water.

1.18 Any of the preceding compositions further comprising glycerine.

1.19 Any of the preceding compositions further comprising polyethylene glycol.

1.20 Any of the preceding compositions having a pH of about 5 to about 12.

1.21 Any of the preceding compositions having a pH of about 6.1.

1.22 Any of the preceding compositions wherein the dental whitening agent is selected from the group consisting of peroxides, metal chlorites, perborates, percarbonates, peroxyacids, hypochlorites, and combinations thereof.

1.23 Any of the preceding compositions wherein the whitening agent is hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.24 Any of the preceding compositions comprising carbamide peroxide, sodium perborate, sodium percarbonate, and/or hydrogen peroxide.

1.25 Any of the preceding compositions wherein the pH is adjusted with a base selected from triethanolamine, sodium hydroxide, or a basic amino acid.

1.26 Composition 1.25 wherein the basic amino acid is arginine, lysine, citrullene, ornithine, creatine, histidine, diaminobutanoic acid, diaminoproprionic acid, salts thereof and/or combinations thereof.

1.27 Composition 1.25 or 1.26 wherein the basic amino acid is in free or salt form selected from the hydroxide, hydrochloride, bicarbonate, phosphate, and/or combinations thereof.

1.28 Composition 1.27 wherein the basic amino acid is selected from arginine bicarbonate and arginine hydroxide.

1.29 Any of the preceding compositions further comprising a fluoride salt selected from stannous fluoride, sodium fluoride, potassium fluoride, sodium monofluorophosphate, sodium fluorosilicate, ammonium fluorosilicate, amine fluoride, ammonium fluoride, and combinations thereof.

1.30 Any of the preceding compositions comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.31 Any of the preceding compositions which is a gel.

Another embodiment of the present invention is a method for bleaching a patient's tooth comprising applying any one of compositions 1.0-1.31 to a tooth, e.g., as a film. The composition may be allowed to dry, and the dried composition is allowed to adhere to the tooth, e.g., for 1 to 30 minutes before falling or eroding off the tooth surface.

Another embodiment of the present invention includes a method for bleaching a patient's tooth comprising a delivery scaffold which is sized to cover a tooth surface to be bleached coated with any one of compositions 1.0-1.31, positioning the scaffold over the tooth such that at least a portion of composition 1.0-1.31 is in contact with the tooth surface to be bleached, allowing the tray to remain in position over the tooth for at least one hour, and removing the tray from the tooth. The delivery scaffold may be in the form of a tray, wherein the tray is configured to hold a quantity of any one of compositions 1.0-1.31. The delivery scaffold may also be in the form of a strip, e.g., flexible strip wherein compositions 1.0-1.31 form a film on one side of the strip to be applied to the tooth. In another embodiment, the delivery scaffold may be sized to cover more than one tooth.

Other embodiments of the present invention will be apparent to one of skill in the art.

DETAILED DESCRIPTION OF THE INVENTION

An "effective amount" is an amount that is sufficient to have a desired therapeutic or prophylactic effect in the oral cavity without undue adverse side effects such as irritation or allergic response.

Unless otherwise indicated, as used herein, a basic amino acid includes a basic amino acid in free base or salt form.

Dental whitening agents are known in the art, and include any material safe for use in the oral cavity which provides bleaching or stain removal. Suitable agents are peroxides, metal chlorites, perborates, percarbonates, peroxyacids, and combinations thereof. Suitable peroxide compounds include hydrogen peroxide, calcium peroxide, carbamide peroxide, and mixtures thereof. Suitable metal chlorites include calcium chlorite, barium chlorite, magnesium chlorite, sodium chlorite, and potassium chlorite. Suitable hydrogen peroxide sources include, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes. Effective concentrations of dental whitening agents are also known in the art, as are effective treatment times.

The basic amino acids which can be used in the compositions of the present the invention include not only naturally occurring basic amino acids, such as arginine, lysine, and histidine, but also any basic amino acids having a carboxyl group and an amino group in the molecule. Accordingly, basic amino acids include, but are not limited to, arginine, lysine, citrullene, ornithine, creatine, histidine, diaminobutanoic acid, diaminoproprionic acid, salts thereof or combinations thereof. In a particular embodiment, the basic amino acids are selected from arginine, citrullene, and ornithine, preferably, arginine, for example, l-arginine.

As used herein, reference to a basic amino acid also includes salts thereof. As the compositions and devices of the invention are intended for use in the mouth, salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

The compositions of the present invention comprise an effective amount of a basic amino acid. Thus, the composition may comprise from about 1% to about 50% by weight of a basic amino acid, e.g., about 1, 2, 3, 4, 5, 10, 15, 20, 25, 30, 35, 40 or 45%.

The compositions of the present invention may optionally be suspended in a matrix. Suitable matrix materials are safe for use in the oral cavity, and do not readily dissolve in the oral cavity, and do not react with the dental whitening agent or basic amino acid.

Matrix materials are known in the art, and are generally water swellable polymers, such as carboxypolymethylene, carboxymethyl cellulose, carboxypropyl cellulose, poloxamer, carrageenan, Veegum, carboxyvinyl polymers, polyvinylpyrrolidone, and natural gums such as gum karaya, xanthan gum, Guar gum, gum arabic, gum tragacanth, and mixtures thereof.

One preferred matrix material is carboxypolymethylene. It has been previously determined that supersaturated carboxypolymethylene water compositions having a carboxypolyethylene concentration of from about 3.5% to about 12% have a high viscosity, and sustained release dental compositions may be prepared from it. As the compositions of the present invention may have non-aqueous or water insoluble components, the concentration of carboxypolymethylene may be higher, e.g., from about 15% to about 35%.

Carboxypolymethylene may be available from various sources, including from B.F. Goodrich Company under the trade name CARBOPOL, such as CARBOPOL 934P and CARBOPOL 940.

It has been found that carboxypolymethylene may be mixed with glycerine to enable large quantities of carboxypolymcthylene to be dispersed in water. The amounts of glycerine in such compositions is known in the art, e.g., from about 20% to about 70% by weight. Glycerine may optionally be substituted with polypropylene, sorbitol, polyethylene glycols, or other polyols.

The presence of carboxypolymethylene may lower the pH of the compositions of the present invention. To prevent low pH's which may erode dental enamel and to take advantage of the benefits of the basic amino acid, compositions of the present invention may have a pH in the range of from about 5 to 12, e.g., about 5.5 to about 6.5, e.g., about 6.1. The pH of the compositions may be adjusted with any base known in the art to be physiologically acceptable at the intended final concentrations, e.g., sodium hydroxide or triethanolamine, or with a basic amino acid or salt thereof.

Another preferred matrix is polyvinylpyrrolidone, see U.S. Pat. No. 6,730,316, the contents of which are herein incorporated by reference.

Preferably, the basic amino acid and any other ingredients are evenly distributed in the matrix, even if such materials are insoluble in the matrix.

The compositions of the present invention are suitable for directly applying to one or more teeth, e.g., as a thin film. The film is allowed to adhere to the tooth, and is maintained on the tooth surface for 1 to 30 minutes before falling or eroding off.

The compositions of the present invention may be applied to one of more teeth by a delivery scaffold, such as a tray or a strip, both of which are known in the art.

Where the delivery scaffold is a dental tray, the tray is configured to hold a quantity of any one of compositions of the present invention, e.g., from about 0.5 to about 5 ml. Dental trays are known in the art, as are their methods of manufacture. Generally, the dental tray is shaped to be able to fit in a wearer's mouth, and a channel adapted to fit over one or more teeth. Compositions of the present invention are generally dispensed into the channel, and then the dental tray is adhered to the teeth.

Where the delivery scaffold is a strip, the tooth whitening compositions of the present invention may be applied or coated onto the strip. Such dental strips are known in the art, as are methods for their manufacture. Strips generally have a flexibility and stiffness which enables them to bend and conform to form a curved shape around one tooth or a plurality of adjacent teeth. The strip may also have shallow pockets to provide a reservoir of the bleaching composition. Generally, the viscous and adhesive nature of the beaching composition allows for the strip to be reversibly attached to one or adjacent teeth. However, the adhesiveness is low enough to allow the strip to be easily removed by the wearer by pulling off the strip of material.

In one embodiment of the present invention, the compositions may optionally include an effective amount of fluoride, or a fluoride ion source, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof.

In certain embodiments, the oral care composition of the invention may also contain a source of fluoride ions or fluorine-providing ingredient in amounts sufficient to supply about 25 ppm to 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A mouthwash, for example, would typically have about 100 to about 250 ppm fluoride. A toothpaste for general consumer use would typically have about 1000 to about 1500 ppm, with pediatric toothpaste having somewhat less. A dentifrice or coating for professional application could have as much as 5,000 or even 25,000 ppm fluoride.

Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt In another embodiment of the present invention, the compositions may optionally comprise an antiseptic, antimicrobial or antibacterial agent, the agent being selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing, to further aid in the beneficial effects of the basic amino acid.

The compositions may further comprise an agent that interferes with or prevents bacterial attachment, e.g., solbrol or chitosan In another embodiment of the present invention, the compositions may optimally comprise anti-inflammatory agents, such as non-steroid anti-inflammatory drugs.

The compositions of the present invention may also include flavors. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Useful flavorings may also include sweeteners, such as sucralose, aspartaine, saccharine. The compositions of the present invention may also include colors.

Enhancing oral health also provides benefits in systemic health, as the oral tissues can be gateways for systemic infections. Good oral health is associated with systemic health, including cardiovascular health. The compositions and methods of the invention provide particular benefits because basic amino acids, especially arginine, are sources of nitrogen which supply NO synthesis pathways and thus enhance microcirculation in the oral tissues. Providing a less acidic oral environment is also helpful in reducing gastric distress and creates an environment less favorable to *Heliobacter*, which is associated with gastric ulcers. Arginine in particular is required for high expression of specific immune cell receptors, for example 'l'-cell receptors, so that arginine can enhance an effective immune response. The compositions and methods of the invention are thus useful to enhance systemic health, including cardiovascular health.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1

A dental bleaching composition is prepared by combining the following ingredients:

| | |
|---|---|
| Dental whitening agent | 10% |
| Basic amino acid | 50% |
| Water | 40% |

Example 2

25 grams of L-arginine is added to 50 grams of water to form a slurry. 5 grams of a 10% carbamide peroxide solution is added to the slurry, and the slurry is applied to an extracted tooth in vitro. The composition is rinsed away following 2 hours of treatment, and the tooth appears to be whiter in color when compared to a shade guide.

Example 3

25 grams of L-arginine bicarbonate is added to 50 grams of water to form a solution. 5 grams of a 10% carbamide peroxide solution is added to the solution, and a stained extracted tooth from a smoker (approximately 25 cigarettes per day, without visiting a dental hygienist for S months) is immersed therein in vitro. The composition is rinsed away following 2 hours of treatment, and the tooth appears to be whiter in color when compared to a shade guide.

Example 4

A dental bleaching composition is prepared by combining the following ingredients

| | |
|---|---|
| Carbamide peroxide | 10% |
| Water | 21% |
| Glycerine | 57% |
| CARBOPOL 934P | 7% |
| L-arginine | 5% |

Example 5

The composition of EXAMPLE 4 is adjusted to a pH of 10 with a concentrated sodium hydroxide solution.

Example 6

The composition of EXAMPLE 4 is adjusted to a pH of 9 with a 40% solution of arginine hydroxide.

Example 7

The composition of EXAMPLE 4 is adjusted to a pH of 8 with a 60% solution of arginine bicarbonate.

Example 8

1 gram of triclosan is added to 99 g of the composition of EXAMPLE 4 or 7.

Example 9

The composition of EXAMPLE 4, 5, 6, 7 and 8 is added to a dental tray in a sufficient amount to cover teeth. The tray is affixed to the upper teeth of a patient for 3 hours and then removed. Teeth treated with the composition are judged to be whiter following treatment when comparing to a shade guide.

Example 10

A liquid whitening gel composition is prepared by combining the following ingredients:

| Liquid Whitening Gel Base Formula | |
|---|---|
| Ingredient | % by weight |
| Water | q.s. |
| Carbopol | 1.00 |
| 95% Ethyl Alcohol | 34.80 |
| Glycerin | 5.00 |
| PEG 600 | 10.00 |
| PEG 2M | 14.00 |
| Hydrogen Peroxide | 25.00 |
| 85% Phosphoric acid | 0.05 |
| Monobasic sodium phosphate | 0.05 |
| Arginine phosphate | 5 |
| Total | 100 |

Example 11

A pressure sensitive whitening adhesive gel composition is prepared by combining the following ingredients:

| Composition Ingredients | A | B |
|---|---|---|
| BIO Pressure Sensitive Silicone Adhesive (medium/high tack)* | 30.0 | 30.0 |
| Plastigel | 34 | 34 |
| Sodium percarbonate | 25 | — |
| PVP H2O2 cx** | — | 25.0 |
| Saccharin | 0.8 | 0.50 |
| Flavor | 14.00 | |
| PEG 400 | — | — |
| Polyisobutente | — | — |
| Arginine bicarbonate | 10.0 | 10.0 |

*Dissolved in 60% by weight dimethicone
**cx = crossed-linked

The invention claimed is:

1. A composition comprising an effective amount of a dental whitening agent, and from about 0.1% to about 50% by weight of arginine in salt form; and the composition further comprising a matrix material wherein the dental whitening agent and arginine are dispersed within said matrix material; and wherein the matrix material comprises carboxypolymethylene;
   wherein the arginine salt comprises arginine phosphate, and
   wherein the composition has a pH of about 5.5 to about 6.5.
2. The composition of claim 1 wherein the arginine salt further comprises arginine hydrochloride.
3. The composition of claim 1 wherein the arginine salt further comprises arginine percarbonate.
4. The composition of claim 1 wherein the arginine salt further comprises arginine bicarbonate.
5. The composition of claim 1 wherein said matrix material further comprises polyvinylpyrrolidone.
6. The composition of claim 1 further comprising glycerine.
7. The composition of claim 1 further comprising polyethylene glycol.
8. The composition of claim 1 having a pH of 6.1.
9. The composition of claim 1 wherein the dental whitening agent is selected from the group consisting of peroxides, metal chlorites, perborates, percarbonates, peroxyacids, and combinations thereof.
10. The composition of claim 9 wherein the dental whitening agent is selected from the group consisting of carbamide peroxide, sodium perborate, sodium percarbonate, hydrogen peroxide, and combinations thereof.
11. The composition of claim 1 further comprising triethanolamine, sodium hydroxide, or a basic amino acid.
12. The composition of claim 11 wherein the basic amino acid is selected from the group consisting of lysine, citrulline, ornithine, creatine, histidine, diaminobutanoic acid, diaminoproprionic acid, salts thereof and combinations thereof.
13. The composition of claim 11 wherein the basic amino acid is in salt form, and the salt form is selected from the group consisting of a hydroxide, a peroxide, a bicarbonate, and combinations thereof.
14. The composition of claim 1 further comprising a fluoride ion source selected from the group consisting of stannous fluoride, sodium fluoride, potassium fluoride, sodium monofluorophosphate, sodium fluoro silicate, ammonium fluorosilicate, amine fluoride, ammonium fluoride, and combinations thereof.
15. The composition of claim 1 further comprising an antibacterial agent selected from the group consisting of a halogenated diphenyl ether, herbal extracts and essential oils, bisguanide antiseptics, quaternary ammonium compounds, phenolic antiseptics, hexetidine, octenidine, sanguinarine, povidone iodine, delmopinol, salifluor, metal ions, sanguinarine, propolis and oxygenating agents, phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidine derivatives, nicin preparations, chlorite salts, and mixtures of any of the foregoing.

16. The composition of claim 1, wherein the composition is in the form of a gel.

17. A device for bleaching a patient's tooth comprising
a delivery scaffold which is sized to cover a tooth surface; and
the composition of claim 1;
wherein said scaffold is coated with said composition of claim 1.

18. The device of claim 17 wherein the scaffold is a dental tray.

19. The device of claim 17 wherein the scaffold is a strip.

20. A method for bleaching a tooth comprising
coating a scaffold which is sized to cover a tooth surface with the composition of claim 1,
positioning the scaffold over the tooth such that at least a portion of the composition is in contact with the tooth surface,
maintaining the tray in position over the tooth for at least one hour, and
removing the tray from the tooth.

21. The composition of claim 11, having a pH of about 6.1.

22. The composition of claim 1, further comprising a potassium ion source.

23. The composition of claim 22, wherein said potassium ion source is selected from the group consisting of potassium nitrate and potassium chloride.

* * * * *